United States Patent [19]

Yoshida et al.

[11] Patent Number: 4,973,582

[45] Date of Patent: Nov. 27, 1990

[54] ARTIFICIAL LUNG SURFACTANT AND REMEDY FOR RESPIRATORY DISTRESS SYNDROME CONTAINING IT AS ACTIVE PRINCIPLE

[75] Inventors: Tsunemasa Yoshida; Masayuki Kokubo; Yoshinori Takada, all of Tokyo; Tsutomu Kobayashi, Ishikawa, all of Japan

[73] Assignee: Teijin Limited, Osaka, Japan

[21] Appl. No.: 56,298

[22] Filed: May 29, 1987

Related U.S. Application Data

[63] Continuation-in-part of Ser. No. 521,809, Aug. 10, 1983, abandoned.

[30]    Foreign Application Priority Data

Nov. 22, 1982 [JP] Japan .................................. 57-203684
Mar. 1, 1983 [JP] Japan .................................. 58-31752

[51] Int. Cl.$^5$ ............................................ A61K 31/685
[52] U.S. Cl. .......................................... 514/78; 514/23
[58] Field of Search ..................................... 514/23, 78

[56]             References Cited

PUBLICATIONS

Colowick et al., *Methods in Enzymology*, vol. XIV, 1969, pp. 276–277.
Freese et al., *Biochim. Biophys. Acta*, 1983, 750(1), pp. 47–89.
King, *Federation Proceedings*, vol. 33, No. 11, 1974, pp. 2238–2246.
Morley et al., *The Lancet*, pp. 64–68.
Freeze et al., *Chemical Abstracts*, vol. 98, 1983, No. 47272d.
Tanaka et al., *Chemical Abstracts*, vol. 98, 1983, No. 49063k.

*Primary Examiner*—Johnnie R. Brown
*Assistant Examiner*—Elli Peselev
*Attorney, Agent, or Firm*—Sughrue, Mion, Zinn, Macpeak & Seas

[57]             ABSTRACT

An artificial lung surfactant comprising (a) phosphatidyl choline and cardiolipin and/or phosphatidyl choline and cardiolipin and/or phosphatidyl glycerol in addition as phospholipids, wherein the content of the pospholipids is 80 to 95 wt % of the whole composition, (b) neutral lipids, wherein the content is 5 to 20 wt % of the whole composition, and (c) fatty acids, wherein the content is 0 to 10 wt % of the whole composition, and a remedy for respiratory distress syndrome containing the surfactant as an active principle.

14 Claims, 3 Drawing Sheets

ARTIFICIAL LUNG SURFACTANT AND REMEDY FOR RESPIRATORY DISTRESS SYNDROME CONTAINING IT AS ACTIVE PRINCIPLE

This is a continuation-in-part of application Ser. No. 521,809, filed Aug. 10, 1983, now abandoned.

BACKGROUND OF THE INVENTION

The present invention relates to an artificial lung surfactant having a surface activity similar to a natural lung surfactant and a remedy for respiratory distress syndrome containing said artificial lung surfactant as an active principle.

There exists in alveoli of animal lungs a physiological active substance, which is called a lung surfactant, mainly comprising phospholipid This substance covers the inner walls of the aveoli of the lung to protect the alveolar epitheliums and also performs an important physiological function for animals to maintain their respiratory functioning. More particularly, the lung surfactant is regarded as a substance having a specific surface-active function to change the surface tension of the inner walls of the alveoli of the lung corresponding to the exhalation and inhalation of breath and also contributing to the maintenance of interalveolium functional stability to exercise an antiatelectatic action. After years of research conducted in medical circles with the use of various animals with regard to the lung surfactant, detailed particulars of its activities are now being made clear step by step. It has been made apparent that this active substance contains phospholipids, neutral lipids, protein, etc., as ingredients and that its main constituent is dipalmitoyl lecithin which is known as one of the phospholipids.

T. Fujiwara et al. recently reported that they obtained an artificially prepared lung surfactant having a higher surface activity by adding dipalmitoyl lecithin, etc., to a surfactant recovered from the bovine lung and that they achieved a good result for the therapy of infantile respiratory distress syndrome (IRDS) by the instillation of the said lung surfactant dispersion to the respiratory tracts of premature babies (Pediatric Clinics, Vol. 32, No. 7, p. 1343, 1979).

Also Kobayashi et al. obtained a lung surfactant prepared from an active substance isolated from swine lung washings, in which $Ca^{++}$ was made to coexist to enhance the activity, and successfully achieved a good result for the substitution therapy of IRDS (Journal of Japanese Medical Society for Biological Interface Vol. 12, No.1, 1981).

In these methods, it is intended to extract phospholipid only from the natural lung surfactant following the Folch procedure, wherein organic solvent soluble substances are extracted by use of a mixed solvent consisting of chlorform and methanol, eliminating the foreign protein arising from bovine and swine; however, the elimination is incomplete and the intermixture of foreign protein up to about 1 to 3% in the obtained phospholipid is observed. Also, the existence of protein, which is proper to the lung but different from ordinary serum albumin, in the naturally obtained lung surfactant is recognized by King et al. (King S.Am. J. Phyoiol. 224 788~795, 1973. Fed. Proc. 33 2238~2241, 1974). It is known that this is a liposoluble protein, which is mainly of a molecular weight of 34,000, containing a hydrophobic amino acid in the large quantities. From the facts mentioned in the above, it is considered that in case where a lung surfactant is prepared from lipids extracted from the native lung surfactant according to the Folch procedure, not only desired phospholipid, neutral lipids, etc., but also protein proper to the lung are extracted and the presence of such protein is regarded as inevitable. The existence of such protein in the lung surfactant is not desirable from the medicamental viewpoint, since it give the strong probability of causing the manifestation of antigenecity and side effects including anaphylaxis.

With the purpose of overcoming the abovementioned defects, C. J. Morley et al. attempted the preparation of an artificial lung surfactant containing no foreign protein and succeeded clinically in its application to IRDS (The Lancet, Jan, 10, 1981). However, this artificial surfactant is prepared in the form of a powder containing dipalmitoyl phosphatidyl choline and phosphatidyl glycerol at the weight ratio of 7:3 and its administration is limited to powder administration which presents some technical difficulty in administration to the alveoli.

SUMMARY OF THE INVENTION

As the result of research to develop an artificial lung surfactant which does not contain any foreign protein, has easily obtainable compounds for its ingredients, and possesses a physicochemical property such as a specific surface activity peculiar to the lung surfactant including, for instance, instantaneous dispersibility into the interface between gas and liquid, formability of a stable interfacial layer, and capability of lowering the surface tension to 10 dyne/cm or less, the inventors of the present invention have found that a certain specific compound has a peculiar surface activity and shows an excellent physiological efficacy in tests made in vivo on rabbits, who have undergone pulmonic irrigations and have reached the present invention.

Accordingly, the present invention is directed to an artificial lung surfactant which comprises (a) phosphatidyl choline and also cardiolipin and/or phosphatidyl glycerol in addition to phospholipids, wherein the content of said phospholipids is 80 to 95 wt % of the whole composition, (b) neutral lipids, wherein the content is 5 to 20 wt % of the whole composition, and (c) fatty acids, wherein the content is 0 to 10 wt % of the whole composition, and a remedy for respiratory distress syndrome containing said artificial lung surfactant as an active principle.

DESCRIPTION OF THE PREFERRED EMBODIMENT

Figure 1:
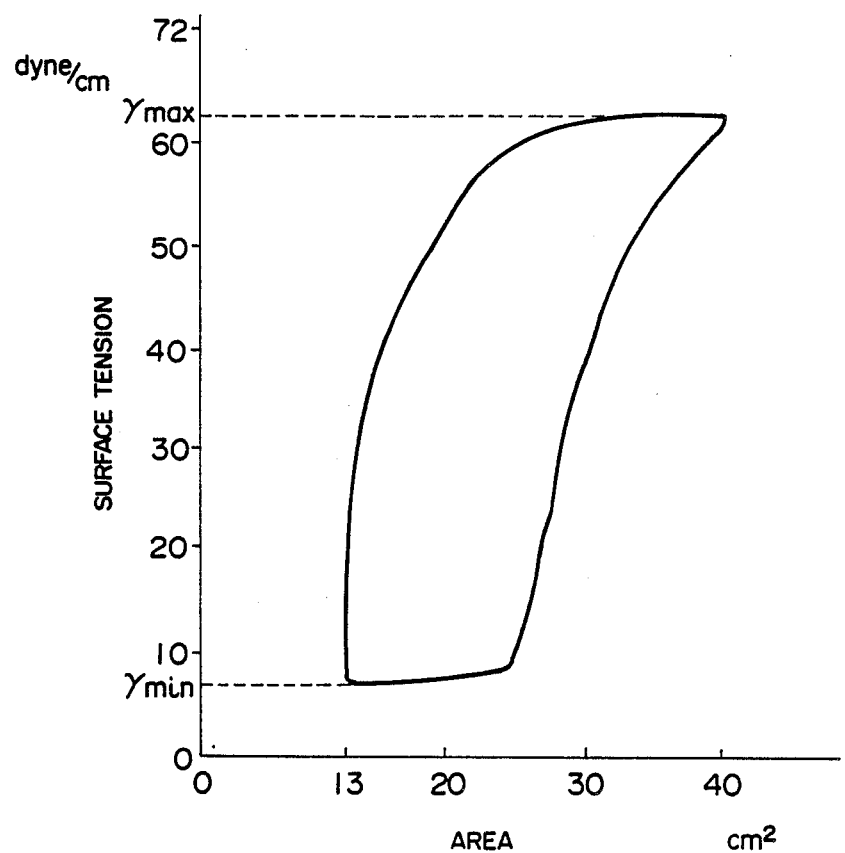
FIG. 1 shows a diagram of surface area versus surface tension of the artificial lung surfactant.

Phosphatidyl choline which is referred to in this invention is a compound expressed by the following formula (I)

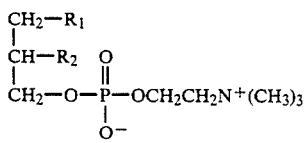
(I)

wherein $R_1$ and $R_2$ indicate saturated straight chain fatty acid residues.

Phosphatidyl choline used in the present invention may be either a native L-substance or artificial DL-substance. As fatty acid residues, those having 14 to 25 carbon atoms are desirable. As examples of them, there are dimyristoyl phosphatidyl choline, dipalmitoyl phosphatidyl choline, distearyl phosphatidyl choline, etc., of which dipalmitoyl phosphatidyl choline is especially desirable.

Cardiolopin used in the present invention is a compound expressed by the following formula (II)

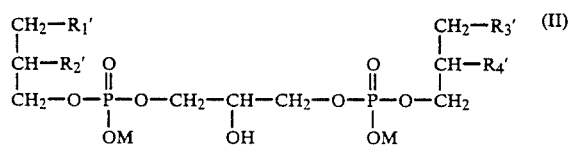
(II)

wherein M is a cation; $R'_1$, $R'_2$, $R'_3$, and $R'_4$ indicate straight chain fatty acid residues. Both native cardiolipin and artificial cardiolipin are usable in the present invention. The native cardiolipin is mainly obtained by extraction from the internal organs such as myocardia, lungs, kidneys, etc. of animals such as bovine, horse, swine, etc., The artificial cardiolipin is obtained synthetically, for instance, according to the method proposed by Van Deenen et al. (Advances in Lipid Research, p. 167, Academic Press (1964)). In both cases, said $R'_1$, $R'_2$, $R'_3$ and $R'_4$ in the formula (II) are straight chain fatty acid residues and it is desirable that part of them are unsaturated ones.

Phosphatidyl glycerol used in the present invention is a compound expressed by the following formula (III)

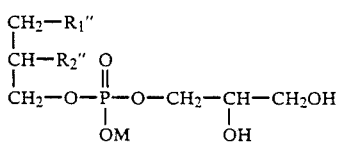
(III)

wherein M denotes a cation; $R''_1$ and $R''_2$ indicate straight chain fatty acid residues.

In the above formula (II) and (III), M denotes a cation such as $H^+$, $Na^+$, $K^+$, $NH_4^+$, $Ca^{++}$.

Phosphatidyl glycerol used in this invention may be either a native L-substance or artificial DL-substance. $R''_1$ and $R''_2$ in the formula (III) should desirably be straight chain fatty acid residues having, 14 to 25 carbon atoms. As example of such saturated fatty acid residues, there are myristic acid residues, palmitic acid residues, stearic acid residues, etc., of which dipalmitoyl phosphatidyl glycerol is especially desirable. As examples of unsaturated fatty acid residues, oleic acid residues and linoleic acid residues may be mentioned.

As neutral lipids used in the present invention, there are triglyceride, diglyceride, monoglyceride, cholesterol derivatives, etc., of which triglyceride or diglyceride, whose main ingredients are saturated straight chain fatty acid residues having 14 to 25 carbon atoms, are desirable. As examples of neutral lipids, there are trimyristin, tripalmitin, tristearin, triarachidin, dimyristin, dipalmitin, distearin, diarachidin, trilinolein, triolein, dilinolein, and diolein.

Fatty acids used in this invention are preferably straight chain fatty acids and, for instance, myristic acid, palmitic acid, stearic acid, arachidic acid, etc., may be mentioned as saturated fatty acids, and oleic acid, elaidic acid, linoleic acid, linolenic acid, etc., may be mentioned as unsaturated fatty acids.

As the phospholipids to be contained in the artificial lung surfactant of the present invention, there are a combination of phosphatidyl choline and cardiolipin, a combination of phosphatidyl choline and phosphatidyl glycerol, and a combination of phosphatidyl choline, cardiolipin, and phosphatidyl glycerol. These phospholipids should represent 80 to 95 wt % of the whole composition, desirably 85 to 90 wt %, the neutral lipids should represent 5 to 20 wt % of the whole composition, desirably 5 to 10 wt %, and the fatty acids should represent 0 to 10 wt % of the whole composition, desirably 0 to 5 wt %. If the abovementioned instructions as to the content of main ingredients are not observed, the object of the present invention can not be achieved.

In the present invention, it is especially desirable to have the artificial lung surfactant contain phosphatidyl choline, which possesses two saturated straight chain fatty acid residues having 14 to 25 carbon atoms, representing 55 to 80 wt % of the whole composition, phosphatidyl glycerol, which possesses two straight chain fatty acid residues having 14 to 25 carbon atoms, representing 10 to 35 wt % of the whole composition, and neutral lipids representing 5 to 20 2t % of the whole composition.

In the present invention, other phospholipids, carbohydrates, etc., may be contained as ingredients in addition to the abovementioned ones to such an extent as not to degrade the surface activity of the artificial lung surfactant.

The artificial lung surfactant of this invention can be obtained by homogeneously mixing said phosphatidyl choline and cardiolipin and/or phosphatidyl glycerol. No limit is set on the method and means of mixing; however, to cite one example, a homogeneous mixture can be prepared easily by dissolving the ingredients in such a common solvent as chloroform, etc., and then removing the solvent from the solution. The artificial lung surfactant thus obtained is usually in a state of a wax and when its surface activity is measured by use of a Wilhelmy balance as mentioned later, its minimum surface tension value is 10 dyne/cm or less and its maximum surface tension value is 36 to 70 dyne/cm. Its stability index is 1.2 or more. These values generate a specific hysteresis loop as shown in FIG. 1 similar to that of a natural lung surfactant to indicate that the obtained artificial lung surfactant has a high surface activity.

Since the artificial lung surfactant of this invention is usually obtained in the state of a wax it is advisable to administer it by dispersing it in water or an electrolytic solution such as saline solution or by forming it into a trituration by use of other medically permissible powders as excipients. The preparation of a dispersion liquid can be achieved by dispersing the waxy surfactant directly in a liquid; however, for reasons of sanitation and preparing procedure, a method is taken wherein a trituration is prepared beforehand by lyophilizing a dispersion liquid of appropriate concentration obtained from said waxy surfactant by addition of excipients, as the case may require, and said trituration is dispersed in water at the time of its administration.

As medically permissible powders, those powders which are water-soluble and innocuous are desirable and then is proper to use it at a ratio of 2 to 50 parts by weight against 1 part by weight of the artificial lung surfactant, especially 5 to 20 parts by weight being recommendable. As desirable powders, amino acids and saccharides may be mentioned because they do not degrade the surface activity. As the amino acids, there are essential amino acids such as glycine, alanine, tryptophane, cystine, etc., and as the saccharides, there are glucose, mannitol, sorbitol, etc.

As the methods of preparing a trituration, it can be prepared simply by thoroughly mixing the artificial lung surfactant with medically permissible powders. However, it is preferable to prepare a trituration by dissolving the surfactant in an organic solvent, to which a proper quantity of fine powder of amino acid was added to obtain a homogeneous dispersion liquid. The obtained dispersion liquid is put into a rotary evaporator, etc., and evaporated to dryness under reduced pressure with rotation and stirring. The obtained powder is further pulverized into a fine powder of uniform particle size to give a desired trituration. In another method of preparing a trituration, the surfactant is dispersed in water or an aqueous solution of salt, etc., uniformly. A prescribed amount of said saccharide or amino acid is dissolved in the obtained dispersion liquid to prepare a homogeneous dispersion solution. The dispersion solution is then lyophilized and the obtained powder is further pulverized into fine powder having an uniform particle size to give a desired trituration. The artificial lung surfactant is made to attach to the surfaces of the powdery substance uniformly and can be used as a preparation having the form of a powder. Since the artificial lung surfactant thus prepared in the form of a powder undergoes no change in its surface activity and has the same degree of surface activity as the natural lung surfactant as mentioned hereinbefore, the trituration of the artificial lung surfactant of this invention can reasonably be expected to have enough efficacy as a remedy for respiratory distress syndrome such as IRDS, etc., when administered by inhalation or nebulization.

In the present invention, the measurement of surface tension and the calculation of the stability index of the artificial lung surfactant were conducted according to the following procedures.

In measuring the surface tension, an improved type of the Wilhelmy balance of Acoma make was used. 50 ml of saline solution was put in the teflon trough of the balance and the surface tension of water was adjusted to 72 dyne/cm. In the case where the specimen was a dispersion liquid, the measurement was made after 50 ml of saline solution used in the adjustment was replaced with 50 ml of specimen dispersion liquid. In case where the specimen was a dry substance or powder, a very small amount of the specimen powder was placed gently on 50 ml of saline solution. The surface film area was compressed cyclically in the range of a maximum of 40 cm$^2$ to a minimum of 13 cm$^2$ at the rate of 0.3 cycle/min. to record a surface area-surface tension diagram as shown in FIG. 1 by use of an X-Y recorder. The minimum surface tension ($\gamma$ min) value, maximum surface tension ($\gamma$ max), and area surrounded by the hysteresis loop were obtained from the hysteresis loop converged invariantly at the 5th or 6th cycling from the start. The stability index (S.I.) was obtained from the following equation:

$$S.I. = \frac{2 \times (\gamma \max - \gamma \min)}{\gamma \max + \gamma \min}$$

The measurement of surface activity in vivo was made according to the method proposed by Kataoka et al. (Journal of Japanese Medical Society for Biological Interface 13 (2) 61 (1982)) by means of lung lavage as follows.

A adult rabbit had its trachea cut open under an anesthetic and was given lung lavage five times at intervals of 10 minutes with 75 ml of saline solution through a tube inserted from the cut opening into the trachea. The lung lavage were conducted by slowly injecting a saline solution and then sucking up to remove it. When 5 minutes passed after the lavage was over, the rabbit was given 10 ml of a dispersion liquid containing 1% artificial lung surfactant obtained in the example of the present invention. The treated rabbit was kept under respiratory control by use of a respirator based on an inspiratory intratracheal pressure of 20 cm of mercury and a PEEP (positive end expiratory pressure) of 3 cm of mercury under pure oxygen. For comparison's sake, the same amount of saline solution was administered according to the same method.

The following Comparison and Examples, in which per cents are by weight, illustrate the invention in detail.

Reference 1

Preparation of natural lung surfactant

A lung surfactant was separated following the procedure mentioned below which was based on the method proposed by M. E. Abrams (J. Appl. Physiol 21, 718-720). 2 kg of bovine lung was cut into tiny pieces, homogenized in 5 l of saline solution in a homogenizer, and filtered through a gauze to obtain an extract. The extract was subjected to low speed centrifugation at a rate of 1,000 rpm for 30 minutes to obtain a supernatant. The obtained supernatant was centrifuged at a high rate of 7,000 rpm for 60 minutes to give a centrifugate. The centrifugate was dispersed in a saturated saline solution (specific gravity 1.21) which had been prepared and cooled beforehand. The dispersion liquid was centrifuged at a rate of 7,000 rpm for 30 minutes and the upper white layer was collected, which was then dialyzed against cooled distilled water and lyophilized to obtain a natural lung surfactant.

In accordance with the procedure proposed by Folch, the obtained natural lung surfactant was dissolved in a mixed solvent of chloroform and methanol (volume ratio 2:1) and the solution was then allowed to stand in contact with a 0.5 saline solution to obtain lipids. It was found that the lipids contained about 2% protein. Its surface activity was as shown in Table 1.

The lipids were solubilized with SDS and subjected to electrophoresis analysis of the polyacrylamide gel, disk type according to the ordinary method. The single band was observed at the mobility of 0.72, from which the molecular weight was assumed to be about 35,000 as compared with the mobility of L-chain and H-chain of the immunoglobulin used as a control in the same electrophoresis analysis.

EXAMPLE 1

650 mg of L-α-dipalmitoyl phosphatidyl choline (DPPC), 250 mg of L-α-dipalmitoyl phosphatidyl glycerol (DPPG), and 100 mg of tripalmitin were mixed and dissolved in 50 ml of chloroform to obtain a homogeneous solution. The solution was placed in a rotary evaporator and evaporated at room temperature under reduced pressure to dryness and dried further at a high degree of vacuum to obtain a white waxy solid substance. 50 mg of the thus obtained solid substance was dispersed homogeneously in 50 ml of saline solution and its surface activity was determined with the use of an improved type of Wilhelmy balance. The result is shown in Table 1. The hysteresis loop was large (i.e. the area was large) and the minimum surface tension ($\gamma$ min) was 10 dyne/cm or less. A homogeneous 1% dispersion liquid of the obtained solid substance was prepared to evaluate its effect in vivo when administered to the rabbits subjected to lung lavage. As seen from FIG. 2, the partial pressure of oxygen (Pa $O_2$) in the blood of the rabbits subjected to lung lavage presented the same rise as the natural lung surfactant to show the recovery of respiratory function.

EXAMPLE 2

600 mg of L-α-DPPC, 300 mg of L-α-DPPG, and 100 mg of tripalmitin were mixed and dissolved in 35 ml of chloroform. The solution was evaporated to dryness according to Example 1 to obtain a white waxy solid substance.

Figure 2:
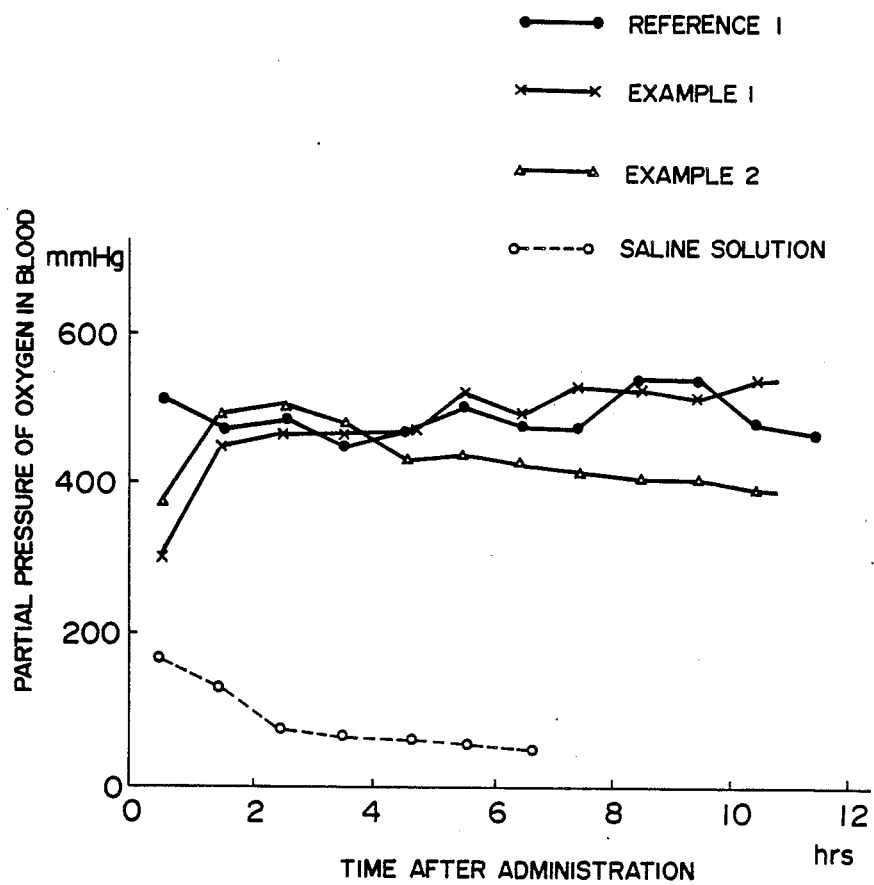
FIG. 2 and FIG. 3 show changes in partial pressure of oxygen in the blood with the passage of time resulting from the administration of the lung surfactant dispersion to the lung lavaged rabbits.

Its surface activity was determined according to Example 1 and the result obtained is shown in Table 1. Thereafter, a homogeneous 1% dispersion liquid of this substance was prepared to evaluate its effect in vivo when administered to rabbits subjected to pulmonic irrigations. As shown in FIG. 2, the partial pressure of oxygen (Pa $O_2$) in the blood presented the same rise as the natural lung surfactant as in Example 1 to show the recovery of respiratory function.

EXAMPLE 3

750 mg of DL-α-DPPC, 150 mg of L-α-DPPG, and 100 mg of tripalmitin were mixed and dissolved in 35 ml of chloroform. A white solid substance was obtained from the solution according to the same procedure as Example 1.

Then 100 mg of this substance was dispersed homogeneously in 50 ml of saline solution and the surface activity was measured with the use of a Wilhelmy balance. The result showed that it had an excellent surface activity as shown in Table 1.

EXAMPLE 4

650 mg of L-α-DPPC, 250 mg of L-α-DPPG, and 100 mg of tristearin were weighed respectively, dissolved in 50 ml of chloroform, and evaporated to dryness to obtain a while waxy substance. The result of the measurement of its surface activity is shown in Table 1 and it showed, a hysteresis loop having a large area and a minimum surface tension ($\gamma$ min) of 10 dyne/cm or less. 500 mg of this substance was dispersed homogeneously in 50 ml of an aqueous solution of 15% mannitol. This dispersion liquid was then lyophilized to obtain a white dry substance. The obtained substance was pulverized in a small-sized ball mill for 20 hours to obtain a fine white powder of uniform particle size. This fine powder had a surface activity as shown in Table 1 and its dispersibility was also very good.

TABLE 1

| | | Surface activity | | | |
|---|---|---|---|---|---|
| Specimen | Form of specimen | Max. surface tension (dyne/cm) | Min. surface tension (dyne/cm) | Stability index | Area ($cm^2$) |
| Reference 1 | Dispersion liquid | 48 | 4 | 1.70 | 24.2 |
| Example 1 | Dispersion liquid | 70 | 6 | 1.68 | 33.4 |
| Example 2 | Dispersion liquid | 65 | 7.5 | 1.59 | 30.6 |
| Example 3 | Dispersion liquid | 62 | 6 | 1.65 | 21.2 |
| Example 4 | Dispersion liquid | 62 | 5 | 1.70 | 26.0 |
| | Powder | 60 | 7 | 1.58 | 25.1 |

EXAMPLE 5

Figure 3:
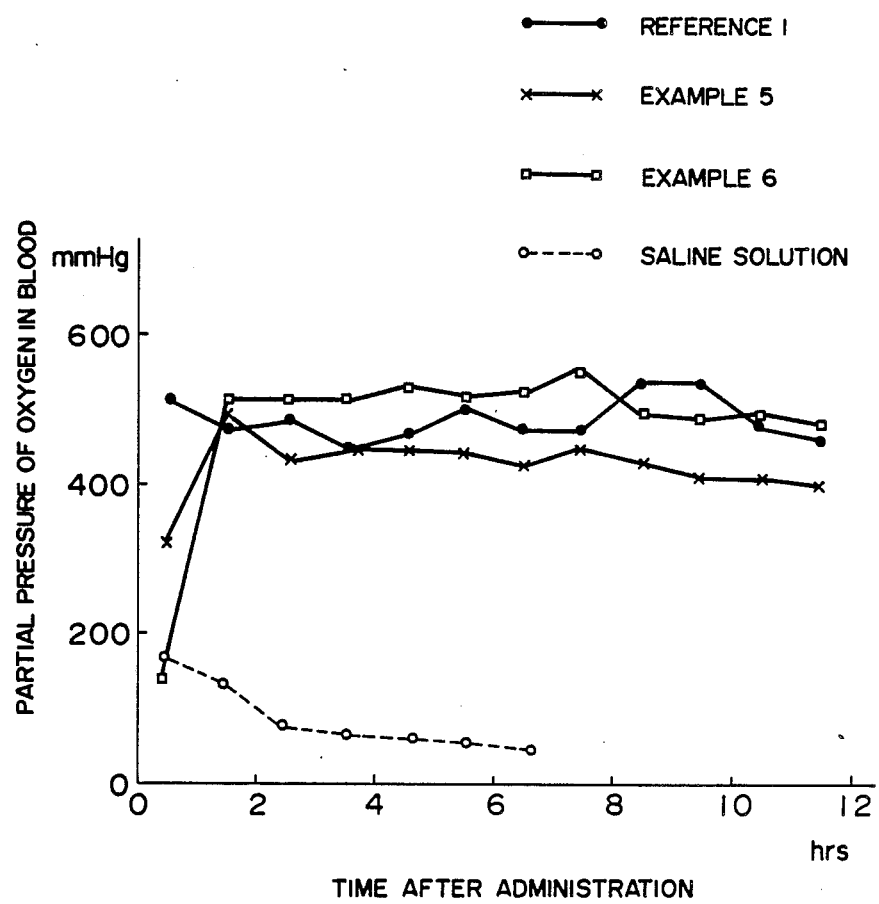

650 mg of L-α-DPPC, 250 mg of the sodium salt of cardiolipin having an iodine value of 77.7 extracted from bovine hearts, and 100 mg of tripalmitin were weighted respectively, mixed, and dissolved in 30 ml of chloroform to prepare a homogeneous solution. The solution was then put in a rotary evaporator and evaporated to dryness at room temperature under reduced pressure, and further dried under high vacuum to obtain a white waxy solid substance. The iodine value of this substance was 19.3. Thereafter, 100 mg of this substance was dispersed homogeneously in 50 ml of saline solution and its surface activity was measured with the use of an improved Wilhelmy balance. When the specimen dispersion liquid was poured in, the surface tension decreased instantly to show an excellent interfacial and adsorbability and it presented a hysteresis loop having a large area. The result is shown in Table 2 indicating that it has a surface activity similar to the natural lung surfactant. Also, a homogeneous 1% dispersion liquid of this substance was prepared to examine its therapeutic effect in vivo by administering it to rabbits subjected to lung lavage along with Reference 1. As shown in FIG. 3, the partial pressure of oxygen (Pa $O_2$) in the blood of the rabbits presented the same rise as the natural one to show the recovery of respiratory function.

EXAMPLE 6

600 mg of L-α-DPPC, 250 mg of cardiolipin, 100 mg of tripalmitin, and also 50 mg of palmitic acid were mixed, dissolved in 30 ml of chloroform, and evaporated to dryness according to Example 5 to obtain a white waxy solid substance. This substance had an iodine value of 19.3 and its surface activity was measured according to Example 5. The result is shown in Table 2.

Then a homogeneous 1% dispersion liquid of this substance was prepared to examine its therapeutic effect in vivo by giving it to rabbits subjected to lung lavage. As seen from FIG. 3, the partial pressure of oxygen (Pa $O_2$) in the blood presented almost the same rise as the natural one to show the recovery of respiratory function.

EXAMPLE 7

550 mg of DL-α-DPPC, 200 mg of ovolecithin (natural phosphatidyl choline), 100 mg of cardiolipin, 75 mg of tripalmitin, and 75 mg of palmitic acid were weighed, dissolved in 30 ml of chloroform, and evaporated to dryness according to Example 5 to obtain a white waxy solid substance. This substance had an iodine value of 23.0. Then, 100 mg of this substance was dispersed homogeneously in 50 ml of saline solution and its surface activity was measured with the use of an improved Wilhelmy balance. The result is shown in Table 2, indicating an excellent surface activity.

EXAMPLE 8

650 mg of DL-α-DPPC, 200 mg of phosphatidyl glycerol, which contains unsaturated fatty acid residues having 14 to 25 carbon atoms, arising from egg yolk lecithin, 100 mg of tripalmitin, and 50 mg of trilinolein were weighed respectively, dissolved in 30 ml of chloroform, and evaporated to dryness according to Example 5 to obtain a yellowish white waxy solid substance. The iodine value of this substance was 24.1.

A 0.2% dispersion liquid of this substance was prepared to measure its surface activity by using a Wilhelmy balance according to Example 5. The result is shown in Table 2, indicating that it has an excellent surface activity.

EXAMPLE 9

600 mg of L-α-DPPC, 300 mg of cardiolipin, and 100 mg of tripalmitin were weighed, dissolved in 30 ml a mixed solvent of chloroform and methanol (volume ratio 2/1), and evaporated to dryness to obtain a white waxy substance. It had an iodine value of 28.0 and the result of the measurement of its surface activity is shown in Table 2. It had an excellent adsorbability and have a hysteresis loop having a large area. Also, 500 mg of this substance was dispersed homogeneously in 50 ml of water, in which 10 g of mannitol was dissolved, to prepare a homogeneous dispersion solution. The dispersion solution was lyophilized to obtain a white dry substance. This substance was subjected to pulverization in a small-sized ball mill for 15 hours to give a white pulverulenta of uniform particle size. It had a surface activity as shown in Table 2 and its dispersibility was also very good.

TABLE 2

| Specimen | Form of specimen | Max. surface tension (dyne/cm) | Min. surface tension (dyne/cm) | Stability index | Area (cm²) |
|---|---|---|---|---|---|
| Example 5 | Dispersion liquid | 46 | 2 | 1.83 | 27.4 |
| Example 6 | Dispersion liquid | 48 | 6 | 1.56 | 24.4 |
| Example 7 | Dispersion liquid | 39 | 8 | 1.32 | 20.3 |
| Example 8 | Dispersion liquid | 60 | 7 | 1.58 | 25.3 |
| Example 9 | Dispersion liquid | 40 | 6 | 1.48 | 20.2 |
|  | Powder | 40 | 4 | 1.64 | 22.8 |
| Example 10 | Waxy solid | 48 | 4 | 1.7 | 24.5 |
|  | Powder | 45 | 5 | 1.6 | 24.0 |

EXAMPLE 10

650 mg of L-α-DPPC, 300 mg of the sodium salt of cardiolipin, and 50 mg of dilinolein were dissolved in 30 ml of chloroform and evaporated to dryness according to Example 5 to obtain a white waxy solid substance. The surface activity of this substance was measured and is shown in Table 2. Furthermore, this waxy solid substance was dispersed homogeneously in 50 ml of an aqueous solution of about 20 wt % mannitol and lyophilized. Thus obtained white lyophile substance was pulverized in a small-sized ball mill at low room temperature for 30 hours to give a white pulverulenta of uniform particle size. The surface activity of this pulverulenta was measured and the result is shown in Table 2. The dispersibility of this substance on the water surface was very good.

What is claimed is:

1. An artificial lung surfactant which consists of (a) phosphatidyl choline of the formula (I):

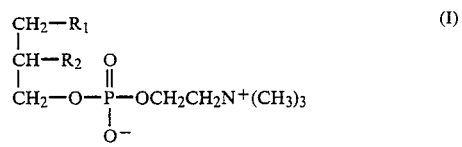

wherein $R_1$ and $R_2$ represent saturated straight chain fatty acid residues having 14 to 25 carbon atoms and also at least one of (i) cardiolipin of the formula (II):

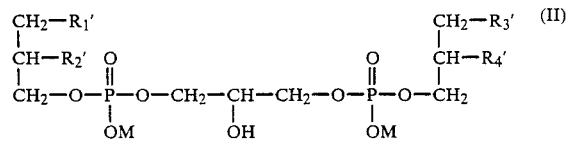

wherein M is a cation; $R'_1$, $R'_2$, $R'_3$ and $R'_4$ represent straight chain fatty acid residues having 14 to 25 carbon atoms and of (ii) phosphatidyl glycerol of the formula (III):

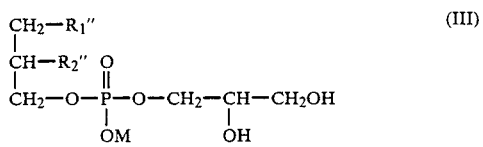

wherein M is cation; $R''_1$ and $R''_2$ represent straight chain fatty acid residues having 14 to 25 carbon atoms in addition as phospholipids, wherein the content of said phospholipids is 80 to 85 wt% of the whole composition, (b) neutral lipids having a saturated straight chain fatty acid residue of 14 to 25 carbon atoms, wherein the content is 5 to 50 wt % of the whole composition, and (c) straight chain fatty acids having 14 to 25 carbon atoms, wherein the content is 0 to 10 wt % of the whole composition.

2. The artificial lung surfactant according to claim 1, wherein the content of phosphatidyl choline which has 2 saturated straight chain fatty acid residues having 14 to 25 carbon atoms is 55 to 80 wt % of the whole composition, that of phosphatidyl glycerol which has 2 straight chain fatty acid residues having 14 to 25 carbon atoms is 10 to 35 wt % of the whole composition, and that of neutral lipids is 5 to 20 wt % of the whole composition.

3. The artificial lung surfactant according to claim 1, wherein the main ingredients of neutral lipids are triglyceride which has saturated straight chain fatty acid residues having 14 to 25 carbon atoms.

4. A composition for the treatment of respiratory distress improved by a lung surfactant containing (I) an artificial lung surfactant as an active principle, wherein said artificial lung surfactant consists of (a) phospholipids, inclusive of phosphatidyl choline of the formula (I):

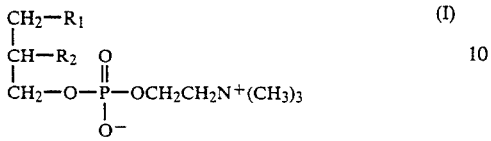

wherein $R_1$ and $R_2$ represent saturated straight chain fatty acid residues having 14 to 25 carbon atoms, and also at least one of (i) cardiolipin of the formula (II):

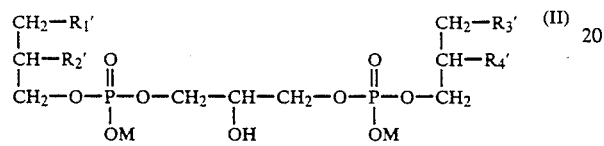

wherein M is a cation; $R'_1$, $R'_2$, $R'_3$ and $R'_4$ represent straight chain fatty acid residues having 14 to 25 carbon atoms and of (ii) phosphatidyl glycerol of the formula (III):

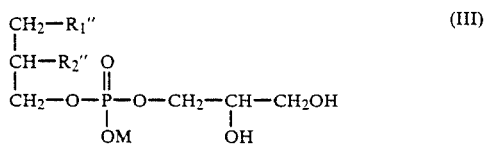

wherein M is a cation; $R''_1$ and $R''_2$ represent straight chain fatty acid residues having 14 to 25 carbon atoms, as constituting 80 to 95 wt % of the whole surfactant, (b) neutral lipids having 14 to 25 carbon s atoms as constituting 5 to 20 wt % of the whole surfactant, and (c) straight chain fatty acids having 14 to 25 carbon atoms as constituting 0 to 10 wt % of the whole surfactant, and (II) a medically permissible excipient.

5. The composition according to claim 4, wherein said artificial lung surfactant is dispersed in water or such an electrolytic solution as saline solution, etc.

6. The composition according to claim 4, wherein said composition comprises the artificial lung surfactant and amedically permissible water-soluble powdery substances in the mixing ratio of 1 part by weight to 2 to 50 parts by weight.

7. The composition according to claim 6, wherein said water-soluble powdery substances are essential amino acids, saccharoses, or mixtures thereof.

8. An artificial lung surfactant which consists of (a) phosphatidyl choline of the formula (I):

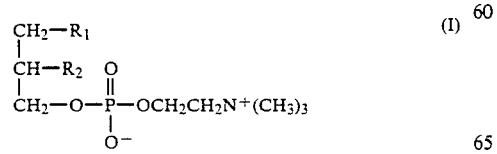

wherein $R_1$ and $R_2$ represent saturated straight chain fatty acid residues having 14 to 25 carbon atoms and also at least one of (i) cardiolipin, the anionic part being of the formula (II):

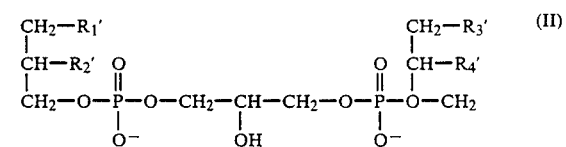

wherein $R'_1$, $R'_2$, $R'_3$ and $R'_4$ represent straight chain fatty acid residues having 14 to 25 carbon atoms and of (ii) phosphatidyl glyceral, the anionic part being of the formula (III):

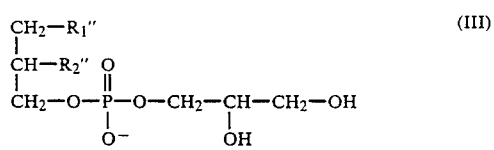

wherein $R''_1$ and $R''_2$ represent straight chain fatty acid residues having 14 to 25 carbon atoms in addition as phospholipids, wherein the content of said phospholipids is 80 to 85 wt % of the whole composition, (b) neutral lipids having a saturated straight chain fatty acid residue of 14 to 25 carbon atoms, wherein the content is 5 to 20 wt % of the whole composition, and (c) straight chain fatty acids having 14 to 25 carbon atoms, wherein the content is 0 to 10 wt % of the whole composition.

9. The artificial lung surfactant according to claim 8, wherein the content of phosphatidyl choline which has 2 saturated straight chain fatty acid residues having 14 to 25 carbon atoms is 55 to 80 wt % of the whole composition, that of phosphatidyl glycerol which has 2 straight chain fatty acid residues having 14 to 25 carbon atoms is 10 to 35 wt % of the whole composition, and that of neutral lipids is 5 to 20 wt % of the whole composition.

10. The artificial lung surfactant according to claim 8, wherein the main ingredients of neutral lipids are triglyceride which has saturated straight chain fatty acid residues having 14 to 25 carbon atoms.

11. A composition for the treatment of respiratory distress improved by a lung surfactant containing (I) an artificial lung surfactant as an active principle, wherein said artificial lung surfactant consists of (a) phospholipids, inclusive of phosphatidyl choline of the formula (I):

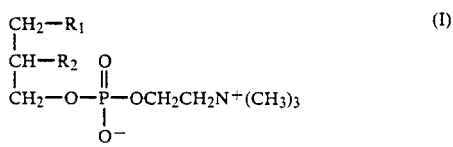

wherein $R_1$ and $R_2$ represent saturated straight chain fatty acid residues having 14 to 25 carbon atoms, and also at least one of (1) cardiolipin the anionic part being of the formula (II):

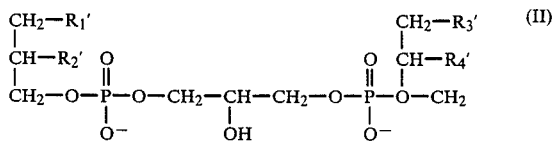

wherein $R'_1$, $R'_2$, $R'_3$ and $R'_4$ represent straight chain fatty acid residues having 14 to 25 carbon atoms and of (ii) phosphatidyl glycerol, the anionic part being of the formula (III):

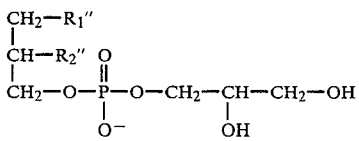

wherein $R''_1$ and $R''_2$ represent straight chain fatty acid residues having 14 to 25 carbon atoms, as constituting 80 to 95 wt % of the whole surfactant, (b) neutral lipids having 14 to 25 carbon atoms as constituting 5 to 20 wt % of the whole surfactant, and (c) straight chain fatty acids having 14 to 25 carbon atoms as constituting 0 to 10 wt % of the whole surfactant, and (II) a medically permissible excipient.

12. The composition according to claim 11, wherein said artificial lung surfactant is dispersed in water or such an electrolytic solution as saline solution.

13. The composition according to claim 11, wherein said composition comprises the artificial lung surfactant and medically permissible water-soluble powdery substances in the mixing ratio of 1 part by weight to 2 to 50 parts by weight.

14. The composition according to claim 13, wherein said water-soluble powdery substances are essential amino acids, saccharoses, or mixtures thereof.

* * * * *